United States Patent [19]

Bernardi et al.

[11] Patent Number: 4,657,914
[45] Date of Patent: Apr. 14, 1987

[54] ERGOLINE DERIVATIVES

[75] Inventors: Luigi Bernardi; Aldemio Temperilli; Sergio Mantegani, all of Milan; Gabriella Traquandi, Cornate d'Adda; Patricia Salvati, Bologna, all of Italy

[73] Assignee: Farmitalia Carlo Erba S.p.A., Milan, Italy

[21] Appl. No.: 488,168

[22] Filed: Apr. 25, 1983

[30] Foreign Application Priority Data

Apr. 30, 1982 [GB] United Kingdom ............... 8212653

[51] Int. Cl.$^4$ ................. A61K 31/48; C07D 457/02
[52] U.S. Cl. ...................................... 514/288; 546/67
[58] Field of Search ............. 546/67; 544/333, 298, 544/242; 548/247

[56] References Cited

U.S. PATENT DOCUMENTS

| | | | |
|---|---|---|---|
| 3,238,211 | 3/1966 | Camerino et al. | 424/261 |
| 3,296,071 | 1/1967 | Wright | 548/247 |
| 3,732,231 | 5/1973 | Semonsky et al. | 546/67 |
| 3,997,536 | 12/1976 | Boller et al. | 544/242 |
| 4,064,130 | 12/1977 | Semonsky et al. | 424/261 |
| 4,147,789 | 4/1979 | Stütz et al. | 546/67 |
| 4,321,381 | 3/1982 | Mantegani et al. | 546/67 |
| 4,382,940 | 5/1983 | Bernardi et al. | 546/67 |

FOREIGN PATENT DOCUMENTS

| | | | |
|---|---|---|---|
| 2330983 | 1/1974 | Fed. Rep. of Germany | 548/247 |
| 615929 | 3/1980 | Switzerland | 546/67 |
| 628895 | 3/1982 | Switzerland | 546/67 |
| 2056437 | 3/1981 | United Kingdom | 546/67 |

OTHER PUBLICATIONS

Guyton, Arthur, *Textbook of Medical Physiology*, 6th Ed., W. B. Saunders, Philadelphia, (1981), p. 1034.

*Primary Examiner*—Donald G. Daus
*Assistant Examiner*—G. Hendricks
*Attorney, Agent, or Firm*—Oblon, Fisher, Spivak, McClelland & Maier

[57] ABSTRACT

There are provided ergoline compounds of the formula:

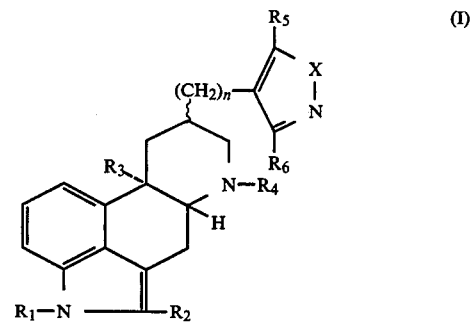

wherein $R_1$ is a hydrogen atom or a methyl group; $R_2$ is a hydrogen or halogen atom, a methyl or thiomethyl group; $R_3$ is a hydrogen atom or a methoxy group; $R_4$ is a hydrocarbon group having from 1 to 4 carbon atoms; n is 1 or 2; each of $R_5$ and $R_6$ independently is a hydrogen atom, an alkyl group having from 1 to 3 carbon atoms, or a phenyl or hydroxy or alkoxy group having from 1 to 4 carbon atoms, and X is an oxygen atom or a group of the formula $NR_7$ wherein $R_7$ is selected from the group consisting of a hydrogen atom, an alkyl having from 1 to 4 carbon atoms and a phenyl group, or a group of the formula $N=C-R_8$ wherein the carbon atom is positioned between the nitrogen atoms in the ring and $R_8$ is an amino, substituted amino, methyl, phenyl, thiomethyl or mercapto group. The compounds have antihypertensive and antiprolactin activity.

4 Claims, No Drawings

ERGOLINE DERIVATIVES

DESCRIPTION OF THE INVENTION

The invention relates to ergoline derivatives, to process for their preparation and to pharmaceutical composition containing them.

The invention provides ergoline compounds of the formula I

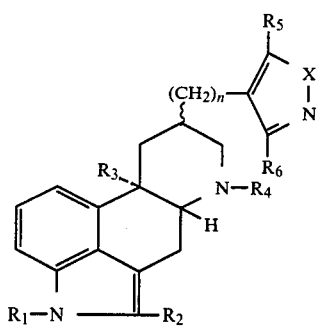

wherein $R_1$ is a hydrogen atom or a methyl group; $R_2$ is a hydrogen or halogen atom, a methyl or thiomethyl group; $R_3$ is a hydrogen atom or a methoxy group; $R_4$ is a hydrocarbon group having from 1 to 4 carbon atoms; n is 1 or 2; each of $R_5$ and $R_6$ independently is a hydrogen atom, an alkyl group having from 1 to 3 carbon atoms, or a phenyl or hydroxy or alkoxy group having from 1 to 4 carbon atoms, and X is an oxygen atom, or a group of the formula $NR_7$ wherein $R_7$ is selected from the group consisting of a hydrogen atom, an alkyl having from 1 to 4 carbon atoms and a phenyl group, or a group of the formula $N=C-R_8$ wherein the carbon atom is positioned between the nitrogen atoms in the ring and $R_8$ is an amino, substituted amino, methyl, phenyl, thiomethyl or mercapto group.

In the definition of $R_4$, a hydrocarbon group having from 1 to 4 carbon atoms is intended to include alkyl, cycloalkyl and unsaturated (both ethylenically and acetylenically) groups.

Representative moieties include methyl, ethyl, n-propyl, isopropyl, butyl, t-butyl, isobutyl, cyclopropyl, methylcyclopropyl, vinyl, allyl and propargyl. The ergoline derivatives according to the invention may be prepared by condensing a β-dicarbonyl ergoline derivative of the general formula II with a compound of the general formula III

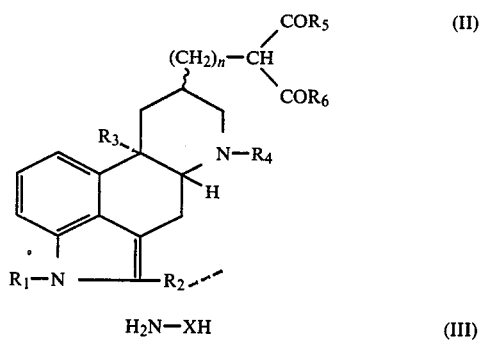

wherein $R_1$, $R_2$, $R_3$, $R_4$, $R_5$, $R_6$, n and X are as above defined. This process is within the scope of the invention.

The condensation process may be carried out in a solvent such as dimethylsulphoxide, ethanol, methanol or acetic acid, with or without addition of a base, such as sodium ethoxide, at a temperature of from 50° to 150° C. for a period of 2 to 24 hours. At the end of the reaction the products may be isolated and purified following conventional procedures, for example chromatography and/or crystallization.

The β-dicarbonyl ergoline derivatives having the general formula II are either known compounds or may be prepared by established procedures starting from known compounds. More particularly we have accomplished their preparation in two ways. The first (method a) involves the reaction in which an ester of 6-alkyl-8-hydroxyalkylergoline is caused to react with a nucleophilic carbanion derived from a β-dicarbonyl compound (see U.S. Pat. No. 4,252,941). Esters useful as starting materials in the above synthetic procedure include the mesyl, p-tosyl and the like esters formed with the hydroxy group of an appropriate 6-alkyl-8-hydroxyalkylergoline. Alternatively (method b) the β-dicarbonyl ergoline derivatives may be prepared by the Knoevenagel reaction between a β-dicarbonyl compound and a 6-alkyl-8β-formyl-ergoline. The β,γ-unsaturated carbonyl compounds which are the major products are then reduced with hydrogen in the presence of a heavy metal catalyst such as a palladium catalyst, to give the products of the general formula II.

The ergoline derivatives according to the invention and their pharmaceutically acceptable salts are useful antihypertensive agents and they display from moderate to good antiprolactinic activity. Accordingly, the invention further provides a pharmaceutical composition comprising an ergoline derivative according to the invention or a pharmaceutically acceptable salt of such an ergoline derivative in admixture with a pharmaceutically acceptable diluent or carrier. The following Examples illustrate the invention.

EXAMPLE 1

6-methyl-8β-(3,5-dimethyl-4-pyrazolylmethyl)-ergoline

A mixture of 3 g of 6-methyl-8β-(3-oxo-2-acetyl-butyl)-ergoline, prepared as described in U.S. Pat. No. 4,252,941, 100 ml of methanol and 3 ml of hydrazine was refluxed for 1 hour. After evaporation to dryness in vacuo the residue was crystallized from methanol to give 2.5 g of the title compound, m.p. >300° C.

EXAMPLES 2 TO 31

Operating as described in Example 1, but using the following β-dicarbonyl and ring closure compounds, the ergoline derivatives (I) listed in the Table 1 were prepared. In the Table 1, melting points are given in degrees centigrade and yields as percentages.

| β-dicarbonyl compounds | Examples |
|---|---|
| +1,6-dimethyl-8β-(3-oxo-2-acetyl-butyl-ergoline (m.p. 165–170° C.) | 2 |
| +6-methyl-10-methoxy-8β-(3-oxo-2-acetyl-butyl)-ergoline (m.p. 163–165° C.) | 3,9–11 |
| +1,6-dimethyl-10-methoxy-8β-(3-oxo-2-acetyl-butyl)-ergoline (m.p. 121–122° C.) | 4,12–15 |
| +6-methyl-8β-(4-oxo-3-acetyl-pentyl)-ergoline (m.p. 160–165° C.) | 5,18–20,30,31 |
| +6-methyl-8β-(3-oxo-2-acetyl-butyl)-ergoline | 6–8,27,29 |
| +6-allyl-8β-(3-oxo-2-acetyl-butyl)- | 16,24,28 |

| | Examples |
|---|---|
| ergoline (m.p. 186-188° C.) +6-propyl-8β-(3-oxo-2-acetyl-butyl)-ergoline (m.p. 200-202° C.) | 17,23 |
| +6-methyl-8β-(3-oxo-2-ethoxycarbonyl-butyl)-ergoline | 21,22 |
| +6-methyl-8α-(3-oxo-2-acetyl-butyl)-ergoline (m.p. 198-200° C.) | 25,26 |

Ring Closure Compound

| | Examples |
|---|---|
| 1,1-dimethyl guanidine | 29,30 |

The ergoline derivatives prepared according to Examples 7 and 23 display good antiprolactinic activity (with an $ED_{50}$ of 0.5 mg/kg os and of less than 4 mg/kg os, respectively).

TABLE 1

| Example | Compound | $R_1$ | $R_2$ | $R_3$ | $R_4$ | $R_5$ | $R_6$ | X | n | m.p. | yield % |
|---|---|---|---|---|---|---|---|---|---|---|---|
| 2 | 1,6-dimethyl-8β-(3,5-dimethyl-4-pyrazolylmethyl)-ergoline | $CH_3$ | H | H | $CH_3$ | $CH_3$ | $CH_3$ | NH | 1 | 238-240 | 86 |
| 3 | 6-methyl-10-methoxy-8β-(3,5-dimethyl-4-pyrazolylmethyl)-ergoline | H | H | H | $CH_3$ | $CH_3$ | $CH_3$ | NH | 1 | 274-276 | 75 |
| 4 | 1,6-dimethyl-10-methoxy-8β-(3,5-dimethyl-4-pyrazolylmethyl)-ergoline | $CH_3$ | H | H | $CH_3$ | $CH_3$ | $CH_3$ | NH | 1 | 282-283 | 83 |
| 5 | 6-methyl-8β-[2-(3,5-dimethyl-4-pyrazolyl)-ethyl]-ergoline | H | H | H | $CH_3$ | $CH_3$ | $CH_3$ | NH | 2 | 234-237 | 40 |
| 6 | 6-methyl-8β-(1,3,5-trimethyl-4-pyrazolyl-methyl)-ergoline | H | H | H | $CH_3$ | $CH_3$ | $CH_3$ | $NCH_3$ | 1 | 168-170 | 75 |
| 7 | 6-methyl-8β-(3,5-dimethyl-4-isoxazolyl-methyl)-ergoline | H | H | H | $CH_3$ | $CH_3$ | $CH_3$ | O | 1 | >300 | 70 |
| 8 | 6-methyl-8β-(2-amino-4,6-dimethyl-5-pyrimidinylmethyl)-ergoline | H | H | H | $CH_3$ | $CH_3$ | $CH_3$ | $N=C-NH_2$ | 1 | 288-290 | 45 |
| 9 | 6-methyl-10-methoxy-8β-(1,3,5-trimethyl-4-pyrazolylmethyl)-ergoline | H | H | $CH_3O$ | $CH_3$ | $CH_3$ | $CH_3$ | $NCH_3$ | 1 | 235-237 | 78 |
| 10 | 6-methyl-10-methoxy-8β-(3,5-dimethyl-4-isoxazolylmethyl)-ergoline | H | H | $CH_3O$ | $CH_3$ | $CH_3$ | $CH_3$ | O | 1 | 229-231 | 60 |
| 11 | 6-methyl-10-methoxy-8β-(2-amino-4,6-dimethyl-5-pyrimidinylmethyl)-ergoline | H | H | $CH_3O$ | $CH_3$ | $CH_3$ | $CH_3$ | $N=C-NH_2$ | 1 | 185-187 | 50 |
| 12 | 1,6-dimethyl-10-methoxy-8β-(1,3,5-trimethyl-4-pyrazolylmethyl)-ergoline | $CH_3$ | H | $CH_3O$ | $CH_3$ | $CH_3$ | $CH_3$ | $NCH_3$ | 1 | 189-190 | 82 |
| 13 | 1,6-dimethyl-10-methoxy-8β-(3,5-dimethyl-4-isoxazolylmethyl)-ergoline | $CH_3$ | H | $CH_3O$ | $CH_3$ | $CH_3$ | $CH_3$ | O | 1 | 190-191 | 85 |
| 14 | 1,6-dimethyl-10-methoxy-8β-(2-amino-4,6-dimethyl-5-pyrimidinylmethyl)-ergoline | $CH_3$ | H | $CH_3O$ | $CH_3$ | $CH_3$ | $CH_3$ | $N=C-NH_2$ | 1 | 210-212 | 45 |
| 15 | 1,6-dimethyl-10-methoxy-8β-(2-phenyl-4,6-dimethyl-5-pyrimidinylmethyl)-ergoline | $CH_3$ | H | $CH_3O$ | $CH_3$ | $CH_3$ | $CH_3$ | $N=C-C_6H_5$ | 1 | 157-158 | 60 |
| 16 | 6-allyl-8β-(3,5-dimethyl-4-isoxazolylmethyl)-ergoline | H | H | H | allyl | $CH_3$ | $CH_3$ | O | 1 | 232-234 | 70 |
| 17 | 6-propyl-8β-(3,5-dimethyl-4-isoxazolylmethyl)-ergoline | H | H | H | $C_3H_7$ | $CH_3$ | $CH_3$ | O | 1 | 207-209 | 75 |
| 18 | 6-methyl-8β-[2-(1,3,5-trimethyl-4-pyrazolyl)-ethyl]-ergoline | H | H | H | $CH_3$ | $CH_3$ | $CH_3$ | $NCH_3$ | 2 | 198-200 | 35 |
| 19 | 6-methyl-8β-[2-(1,3,5-trimethyl-4-isoxazolyl)-ethyl]-ergoline | H | H | H | $CH_3$ | $CH_3$ | $CH_3$ | O | 2 | 235-237 | 45 |
| 20 | 6-methyl-8β-[2-(2-amino-4,6-dimethyl-5-pyrimidinyl)-ethyl]-ergoline | H | H | H | $CH_3$ | $CH_3$ | $CH_3$ | $N=C-NH_2$ | 2 | 233-235 | 48 |
| 21 | 6-methyl-8β-(5-hydroxy-3-methyl-4-pyrazolylmethyl)-ergoline | H | H | H | $CH_3$ | OH | $CH_3$ | NH | 1 | 213-215 | 65 |
| 22 | 6-methyl-8β-(4-hydroxy-2,6-dimethyl-5-pyrimidinylmethyl)-ergoline | H | H | H | $CH_3$ | $CH_3$ | OH | $N=C-CH_3$ | 1 | >300 | 55 |
| 23 | 6-propyl-8β-(3,5-dimethyl-4-pyrazolylmethyl)-ergoline | H | H | H | $C_3H_7$ | $CH_3$ | $CH_3$ | NH | 1 | 268-270 | 75 |
| 24 | 6-allyl-8β-(3,5-dimethyl-4-pyrazolylmethyl)-ergoline | H | H | H | allyl | $CH_3$ | $CH_3$ | NH | 1 | 242-244 | 68 |
| 25 | 6-methyl-8α-(3,5-dimethyl-4-pyrazolylmethyl)-ergoline | H | H | H | $CH_3$ | $CH_3$ | $CH_3$ | NH | 1 | >300 | 65 |
| 26 | 6-methyl-8α-(3,5-dimethyl-4-isoxazolylmethyl)-ergoline | H | H | H | $CH_3$ | $CH_3$ | $CH_3$ | O | 1 | >300 | 62 |
| 27 | 6-methyl-8β-(2-phenyl-4,6-dimethyl-5-pyrimidinylmethyl)-ergoline | H | H | H | $CH_3$ | $CH_3$ | $CH_3$ | $N=C-C_6H_5$ | 1 | 172-174 | 65 |
| 28 | 6-allyl-8β-(2-amino-4,6-dimethyl-5-pyrimidinylmethyl)-ergoline | H | H | H | allyl | $CH_3$ | $CH_3$ | $N=C-NH_2$ | 1 | 247-249 | 53 |
| 29 | 6-methyl-8β-(2-dimethylamino-4,6-dimethyl-5-pyrimidinylmethyl)-ergoline | H | H | H | $CH_3$ | $CH_3$ | $CH_3$ | $N=C-N(CH_3)_2$ | 1 | 197-199 | 58 |
| 30 | 6-methyl-8β-[2-(2-dimethylamino-4,6-dimethyl-5-pyrimidinyl) ethyl]-ergoline | H | H | H | $CH_3$ | $CH_3$ | $CH_3$ | $N=C-N(CH_3)_2$ | 2 | 250-252 | 55 |
| 31 | 6-methyl-8β[2-(2-phenyl-4,6-dimethyl-5-pyrimidinyl)ethyl]-ergoline | H | H | H | $CH_3$ | $CH_3$ | $CH_3$ | $N=C-C_6H_5$ | 2 | 266-268 | 64 |

| | |
|---|---|
| hydrazine | 2-5,21,23,24,25 |
| methylhydrazine | 6,9,12,18 |
| hydroxylamine hydrochloride | 7,10,13,16,17,19,26 |
| guanidine carbonate | 8,11,14,20,28 |
| benzamidine | 15,27,31 |
| acetamidine | 22 |

ANTIHYPERTENSIVE ACTIVITY—METHODS

Indirect measurements of systolic blood pressure were carried out in groups of 4 spontaneously hypertensive rats (SHR, Kyoto), 8-10 weeks of age, supplied by Charles River, Italy.

The animals were maintained in an environment of 36° C. for 10-15 minutes to allow pulse pressure to be recorded and then systolic blood pressure and heart rate were measured by indirect tail cuff method using a W+W, BP recorder, model 8005.

The compounds were given orally, suspended in 5% arabic gum, once a day for 4 consecutive days and measurements were carried out before beginning the treatment and 1 and 5 hours after dosing in both the first and fourth day of treatment. Drug doses refer to the free base.

Controls animals received the vehicle only (0.2 ml/100 g b.w.). As reference standards, hydralazine (1-5 mg/kg p.o) and α-methyl-dopa (30-100 mg/kg p.o.) were also tested. Drug induced changes in systolic blood pressure and heart rate were calculated as differences from the pretreatment values and reported as means.

ANTIHYPERTENSIVE ACTIVITY—RESULTS

Results are reported in Tables 2 and 3.

Basal systolic blood pressure (SBP) and heart rate (HR) of SH-rats were about 200 mm Hg and 350 beats/min respectively; these parameters remained stable troughout the duration of the experiment in vehicle treated rats, whereas our compounds (Examples 1, 6, 7, 8, 21, 22, 23, 24) were very active in reducing SBP in doses ranging from 0.1 to 20 mg/kg p.o.

In particular examples 1, 7, 8 are interesting antihypertensive compounds being active at the dose of 1 mg/kg p.o. without substantially modifying HR.

The antihypertensive effect was long lasting, being still marked 5 hours after dosing in both the first and fourth day of treatment.

Example 23 as well, is very effective at the dose of 1 mg/kg p.o. in lowering SBP in both the 1st and 4th day of treatment; the fall in SBP was paralled by a decrease in HR. A decrease in HR was also noted with example 24 (7.5 mg/kg p.o.). Comparison with the standards showed how all the examples reported in Tables 2 and 3 possess at the doses tested an antihypertensive effect comparable or even greater than hydralazine (5 mg/kg p.o.) and α-methyldopa (100 mg/kg p.o.) without inducing the reflex increase in HR observed with both hydralazine and α-methyldopa.

TABLE 2

Effects on systolic blood pressure (SBP) in SH-rats. Mean differences from pretreatment values (mm Hg) are reported (4 rats for group).

| Compound | Dose (mg. kg$^{-1}$ p.o.) | Changes in SBP (Δmm Hg) | | | |
|---|---|---|---|---|---|
| | | 1st day | | 4th day | |
| | | 1 h post drug | 5 h post drug | 1 h post drug | 5 h post drug |
| Example 1 | 1 | −32 | −47 | −10 | −23 |
| Example 6 | 7.5 | −51 | −38 | −15 | −20 |
| Example 7 | 0.1 | −20 | −32 | −6 | −30 |
| | 1 | −49 | −38 | −25 | −30 |
| Example 8 | 0.5 | −20 | −33 | −14 | −18 |
| | 1 | −31 | −44 | −35 | −39 |
| Example 21 | 5 | −6 | −24 | −26 | −18 |
| | 20 | −34 | −41 | −44 | −58 |
| Example 22 | 20 | −34 | −50 | −7 | −32 |
| Example 23 | 1 | −21 | −47 | −59 | −84 |
| Example 24 | 7.5 | −54 | −14 | −32 | −48 |
| Hydralazine | 1 | −5 | −16 | −5 | −0.3 |
| | 5 | −40 | −20 | −20 | −7 |
| α-methyldopa | 30 | −10 | −20 | −10 | −0.5 |
| | 100 | −10 | −25 | −20 | −25 |

TABLE 2-continued

Effects on systolic blood pressure (SBP) in SH-rats. Mean differences from pretreatment values (mm Hg) are reported (4 rats for group).

| Compound | Dose (mg. kg$^{-1}$ p.o.) | Changes in SBP (Δmm Hg) | | | |
|---|---|---|---|---|---|
| | | 1st day | | 4th day | |
| | | 1 h post drug | 5 h post drug | 1 h post drug | 5 h post drug |
| Vehicle | — | −30 | +2 | −5 | −5 |

TABLE 3

Effects on heart rate (HR) in SH-rats - Mean differences from pretreatment values (beats/min) are reported (4 rats for group)

| Compound | Dose (mg. kg$^{-1}$ p.o.) | Changes in HR (beats/min) | | | |
|---|---|---|---|---|---|
| | | 1st day | | 4th day | |
| | | 1 h post drug | 5 h post drug | 1 h post drug | 5 h post drug |
| Example 1 | 1 | +3 | +20 | −10 | −15 |
| Example 6 | 7.5 | −20 | −30 | −15 | −7 |
| Example 7 | 0.1 | −8 | −7 | −12 | −15 |
| | 1 | −50 | −50 | −20 | −30 |
| Example 8 | 0.5 | −30 | −35 | −10 | −5 |
| | 1 | −20 | −15 | −30 | −40 |
| Example 21 | 5 | +2 | +10 | −15 | −10 |
| | 20 | −30 | −27 | −35 | −32 |
| Example 22 | 20 | +17 | −10 | +5 | −30 |
| Example 23 | 1 | −90 | −77 | −110 | −65 |
| Example 24 | 7.5 | −100 | −122 | −70 | −93 |
| Hydrolazine | 1 | +30 | +35 | +25 | +15 |
| | 5 | +40 | +45 | +18 | +15 |
| α-methyldopa | 30 | +35 | +40 | +45 | +30 |
| | 100 | +70 | +40 | +50 | +10 |
| Vehicle | — | −10 | +7 | −6 | −5 |

What we claim is:

1. Ergoline compounds of formula (I) selected from the group consisting of:
1,6-dimethyl-8β-(3,5-dimethyl-4-pyrazolylmethyl)-ergoline,
6-methyl-8β-[2-(3,5-dimethyl-4-pyrazolyl)-ethyl]-ergoline,
6-methyl-8β-(1,3,5-trimethyl-4-pyrazolylmethyl)-ergoline,
6-methyl-8β-(3,5-dimethyl-4-isoxazolylmethyl)-ergoline,
6-methyl-8β-(2-amino-4,6-dimethyl-5-pyrimidinylmethyl)-ergoline,
6-allyl-8β-(3,5-dimethyl-4-isoxazolylmethyl)-ergoline,
6-propyl-8β-(3,5-dimethyl-4-isoxazolylmethyl)-ergoline,
6-methyl-8β-(3,5-dimethyl-4-pyrazolylmethyl)-ergoline,
6-methyl-8β-[2-(1,3,5-trimethyl-4-pyrazolyl)-ethyl]-ergoline,
6-methyl-8β-[2-(1,3,5-trimethyl-4-isoxazolyl)-ethyl]-ergoline,
6-methyl-8β-[2-(2-amino-4,6-dimethyl-5-pyrimidinyl)-ethyl]-ergoline,
6-methyl-8β-(5-hydroxy-3-methyl-4-pyrazolylmethyl)-ergoline,
6-methyl-8β-(4-hydroxy-2,6-dimethyl-5-pyrimidinylmethyl)-ergoline,
6-propyl-8β-(3,5-dimethyl-4-pyrazolylmethyl)-ergoline,
6-allyl-8β-(3,5-dimethyl-4-pyrazolylmethyl)-ergoline,
6-methyl-8α-(3,5-dimethyl-4-pyrazolylmethyl)-ergoline, 6-methyl-8α-(3,5-dimethyl-4-isoxazolylmethyl)-ergoline, 6-methyl-8β-(2-phenyl-4,6-dimethyl-5-pyrimidinylmethyl)-ergoline, 6-allyl-8β-(2-amino-4,6-dimethyl-5-pyrimidinylmethyl)-ergoline, 6-methyl-8β-(2-dimethylamino-4,6-dimethyl-5-pyrimidinylmethyl)-ergoline, 6-methyl-8β-[2-(2-dimethylamino-4,6-dimethyl-5-pyrimidinyl)-ethyl]-ergoline, and 6-methyl-8β-[2-(2-phenyl-4,6-dimethyl-5-pyrimidinyl)-ethyl]-ergoline.

2. A pharmaceutical composition comprising:
   (a) a pharmaceutically acceptable carrier and/or diluent; and,
   (b) as an active principle, an antihypertensively effective amount of a compound of the formula (I) according to claim 1 or a pharmaceutically acceptable salt thereof.

3. A process for reducing blood pressure, which comprises:
   administering an antihypertensively effective amount of a compound of formula (I) of claim 1 or a pharmaceutically acceptable salt thereof to a hytertensive animal.

4. The method of claim 3, wherein said amount is from 0.1 to 20 mg/kg of body weight.

* * * * *